United States Patent
Shannon, Jr.

(10) Patent No.: US 8,223,925 B2
(45) Date of Patent: Jul. 17, 2012

(54) COMPACT COLLIMATING DEVICE

(75) Inventor: Robert F. Shannon, Jr., Pasco, WA (US)

(73) Assignee: Bruker AXS Handheld, Inc., Kennewick, WA (US)

( * ) Notice: Subject to any disclaimer, the term of this patent is extended or adjusted under 35 U.S.C. 154(b) by 123 days.

(21) Appl. No.: 12/760,889

(22) Filed: Apr. 15, 2010

(65) Prior Publication Data

US 2011/0255662 A1 Oct. 20, 2011

(51) Int. Cl.
*G21K 1/00* (2006.01)

(52) U.S. Cl. .......................... 378/147; 378/84

(58) Field of Classification Search ............. 378/44–49, 378/82, 147, 149, 84–85, 145
See application file for complete search history.

(56) References Cited

U.S. PATENT DOCUMENTS

| | | | |
|---|---|---|---|
| 4,246,488 A | 1/1981 | Hura |
| 4,384,360 A | 5/1983 | Kitadate et al. |
| 4,489,426 A | 12/1984 | Grass et al. |
| 4,694,480 A | 9/1987 | Skillicorn |
| 4,797,907 A | 1/1989 | Anderton |
| 4,856,036 A | 8/1989 | Malcolm et al. |
| 4,910,759 A | 3/1990 | Sharnoff |
| 4,979,198 A | 12/1990 | Malcolm et al. |
| 5,077,771 A | 12/1991 | Skillicorn et al. |
| 5,099,134 A | 3/1992 | Hase et al. |
| 5,111,493 A | 5/1992 | Siedband |
| 5,153,900 A | 10/1992 | Nomikos et al. |
| 5,379,335 A | 1/1995 | Griesmer et al. |
| 5,442,677 A | 8/1995 | Golden et al. |
| 5,631,943 A | 5/1997 | Miles |
| 5,747,821 A | 5/1998 | York et al. |
| 6,282,260 B1 | 8/2001 | Grodzins |
| 6,459,767 B1 | 10/2002 | Boyer |
| 6,661,876 B2 | 12/2003 | Turner et al. |
| 6,690,765 B1 | 2/2004 | Miller |
| 6,744,852 B2 | 6/2004 | Klotz et al. |
| 6,882,701 B2 | 4/2005 | Ferrandino et al. |
| 6,909,770 B2 | 6/2005 | Schramm et al. |
| 7,209,545 B2 | 4/2007 | Radley et al. |
| 7,375,359 B1 | 5/2008 | Grodzins |
| 7,388,207 B1 | 6/2008 | Zeng |
| 7,463,721 B2 | 12/2008 | Harding et al. |
| 7,496,178 B2 | 2/2009 | Turner |
| 2002/0159561 A1* | 10/2002 | Cederstrom ................. 378/84 |
| 2005/0053199 A1 | 3/2005 | Miles |
| 2005/0213709 A1 | 9/2005 | Dinsmore et al. |
| 2005/0226373 A1 | 10/2005 | Trombka et al. |
| 2006/0098779 A1 | 5/2006 | Turner |
| 2007/0230659 A1* | 10/2007 | Turner ........................ 378/63 |
| 2007/0269010 A1 | 11/2007 | Turner |
| 2008/0095318 A1 | 4/2008 | Kantonen et al. |
| 2008/0095319 A1 | 4/2008 | Grodzins et al. |
| 2008/0159475 A1 | 7/2008 | Mazor et al. |
| 2008/0192897 A1 | 8/2008 | Piorek et al. |
| 2009/0220045 A1 | 9/2009 | Grodzins |
| 2009/0257563 A1* | 10/2009 | Karlsson ................... 378/145 |

* cited by examiner

*Primary Examiner* — Hoon Song
(74) *Attorney, Agent, or Firm* — Armstrong Teasdale LLP (57) ABSTRACT

A collimating device is described. The collimating device includes a housing defining an interior surface and an exterior surface of the collimating device. The housing includes an inlet and an outlet and a cavity extending between the inlet and the outlet. The collimating device also includes a plurality of ridges extending from the interior surface of the housing toward a center of the cavity. The plurality of ridges form a plurality of slits within the cavity configured to collimate radiation entering the inlet and exiting the outlet.

25 Claims, 7 Drawing Sheets

COMPACT COLLIMATING DEVICE

BACKGROUND OF THE INVENTION

The subject matter described herein relates generally to analyzing a substance and, more specifically, to performing an analysis of a substance using a portable spectrometer.

Portable spectrometers, also referred to as analyzers, are used to examine the composition of a sample material in a number of applications. For example, portable spectrometers are used for metal identification, detection and identification of hazardous materials or explosives, detection and identification of environmental pollutants, and identification of lead in paint. Portable spectrometers may also be referred to as handheld spectrometers if the portable spectrometer is configured for handheld operation.

Examples of specific portable analyzers include X-ray fluorescence (XRF) spectrometers and ion mobility spectrometers (IMS). XRF spectrometers detect secondary radiation emitted from a sample of material that has been excited by radiation applied to the sample material by the spectrometer. A wavelength distribution of the emitted radiation is characteristic of the elements present in the sample, while the intensity distribution gives information about the relative abundance of the elements in the sample. By means of a spectrum obtained in this manner, an expert typically is able to determine the components, and quantitative proportions of those components, within the examined test sample.

An IMS analyzes ion mobility to determine the composition of a sample material. Ion mobility analysis measures the movement of ionized sample molecules in a uniform electric field through a given atmosphere. Once a spectrum is obtained corresponding to the measured ion mobilities, a composition of the sample material can be determined.

A full-sized laboratory diffraction analyzer typically includes a collimator having three sets of slits or apertures. The slits or apertures are typically defined within plates. Radiation striking the plate beyond the margin of the aperture is deflected or absorbed. The beam projected through the aperture has a cross-sectional shape similar to that of the aperture and a size or diameter controlled by the position and size of the aperture, and the position of the source. More specifically, the first slit is located near the radiation source and defines the spot size. The spot size is, for example, a diameter of a spot on a sample illuminated by the radiation. The second slit is positioned so it slightly cuts into the radiation beam and is of a size similar to the first slit. The first and second slits collimate the source beam. The third slit is located between the second slit and the sample and is of a slightly larger size than the first and the second slits. The third slit removes the scattered radiation that is emitted from the second slit.

Typically, the size of such a three-slit collimator prohibits use in a portable analyzer, and even more so, in a handheld analyzer. A portable analyzer may use a pipe or a tube that defines an opening to direct generated radiation toward the sample. In the case of an XRF spectrometer, the pipe or tube is typically more for shielding all but the sample from the generated radiation than it is an attempt to collimate the generated radiation. For analyzers that include a laser source, an external collimator may be used to control the spot size, but collimation is unnecessary since the emitted radiation is inherently well collimated.

Furthermore, a typical three-slit collimator is not suitable for use in a portable or handheld analyzer because the three-slit collimator increases a distance between the radiation source and the sample. More power is required to maintain a flux at the sample as the distance between the radiation source and the sample increases. Therefore, it is generally beneficial, especially in portable or handheld analyzers where available power may be limited to power provided by a battery, to minimize the distance between the radiation source and the sample. For similar reasons, the detector is also positioned close to the sample.

The field of view of a detector with this type of geometry is typically large. Such small distances between the radiation source and the sample may cause problematic XRF scattering, Compton and Rayleigh back scatter that increases background noise, Bragg peaks that are not consistent from sample to sample, as well as sample orientations that result in fictitiously high results. Additionally, scattered radiation from the collimator may excite atoms present in the instrument and the resulting fluorescence may be received at the detector, causing an inaccurate reading.

BRIEF DESCRIPTION OF THE INVENTION

In one aspect, a collimating device is provided. The collimating device includes a housing defining an interior surface and an exterior surface of the collimating device. The housing includes an inlet and an outlet and a cavity extending between the inlet and the outlet. The collimating device also includes a plurality of ridges extending from the interior surface of the housing toward a center of the cavity. The plurality of ridges form a plurality of slits within the cavity configured to collimate radiation entering the inlet and exiting the outlet.

In another aspect, a method of collimating radiation output by a radiation source is provided. The method includes providing a radiation source for generating radiation and positioning a collimating device between the radiation source and a sample. The collimating device includes an interior surface that defines a cavity. The cavity includes a plurality of ridges extending from the interior surface toward a center of the cavity. The plurality of ridges define a plurality of slits configured to facilitate reducing scattering of radiation exiting the collimating device.

In yet another aspect, a detection system is provided. The system includes a radiation source configured to generate a primary radiation and impinge the primary radiation onto a sample. The primary radiation is configured to excite the sample and cause the sample to reflect a secondary radiation. The system also includes a radiation detector configured to detect the secondary radiation. The system also includes a collimating device positioned between the radiation source and the sample. The collimating device includes a housing that defines a cavity extending between an inlet and an outlet of the collimating device. The collimating device includes a plurality of ridges extending from the housing toward a center of the cavity, the plurality of ridges defining a plurality of slits configured to facilitate reducing scattering of radiation exiting the outlet of the collimating device.

In yet another aspect, a collimating device is provided. The collimating device includes a housing defining an interior surface and an exterior surface of the collimating device. The housing includes an inlet and an outlet and a cavity extending between the inlet and the outlet. The collimating device also includes a spiraling ridge extending from the interior surface of the housing toward a center of the cavity. The spiraling ridge begins at the inlet and ends at the outlet. The spiraling ridge includes a first surface configured to collimate radiation entering the inlet and exiting the outlet.

DETAILED DESCRIPTION OF THE INVENTION

The methods, systems, and devices described herein facilitate reducing scatter of radiation applied to a sample during testing of the sample. The methods, systems, and devices described herein reduce scatter without increasing a distance between a radiation source and the sample. A reduction in scattered radiation facilitates reducing unwanted Bragg peaks, reducing X-ray florescence (XRF), Compton and/or Rayleigh back scatter, and reducing excitation of atoms present in the instrument that may result in fluorescence detectable by the detector. Maintaining the distance between the radiation source and the sample prevents having to increase the power provided to the radiation source to counteract the additional distance needed to apply collimation of the radiation applied to the sample.

Figure 1:
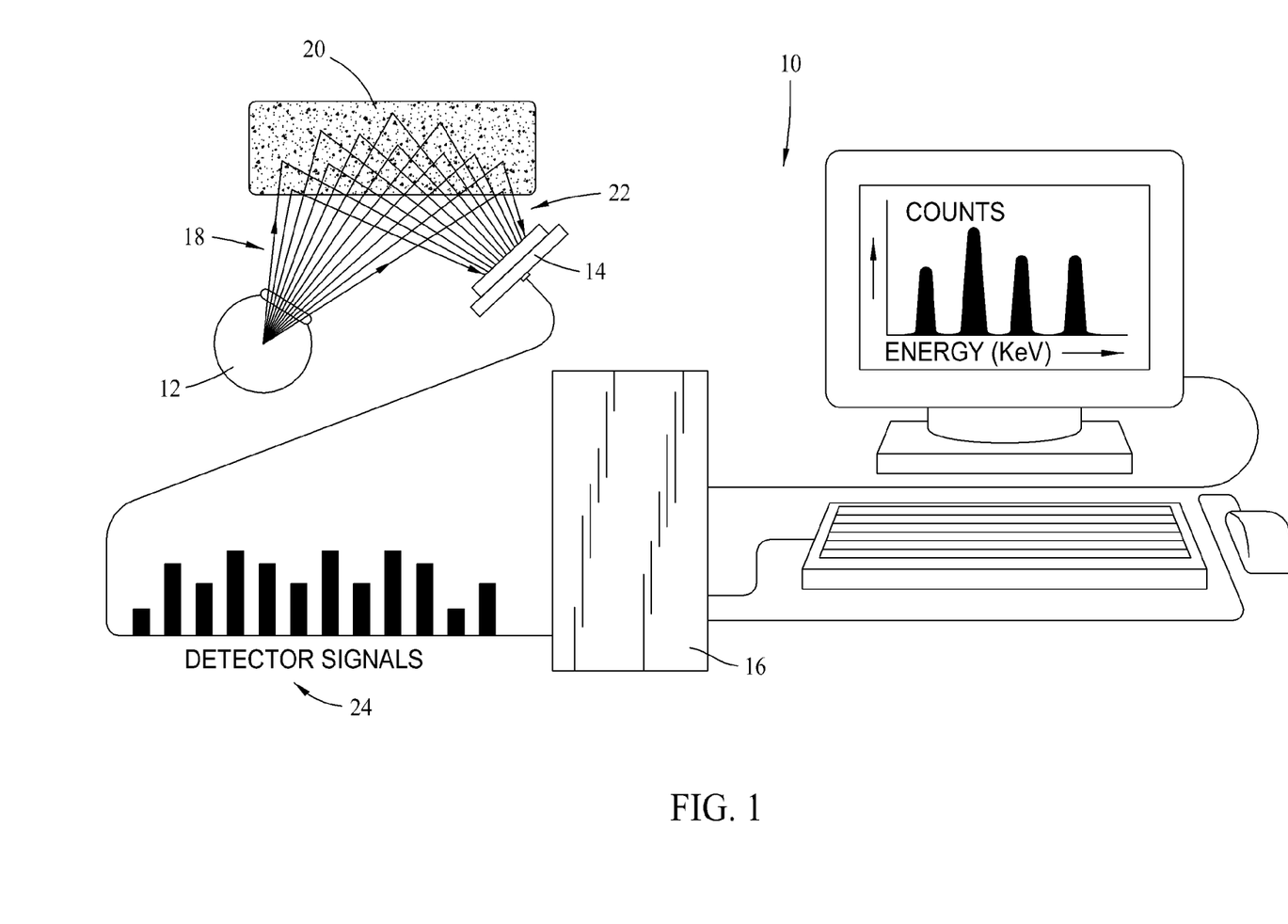
FIG. 1 is a functional illustration of the general components of a detection system.

FIG. 1 is a functional illustration of the general components of a detection system 10, for example, but not limited to, an X-ray fluorescence (XRF) spectrometer or an ion mobility spectrometer (IMS). In the illustrated embodiment, detection system 10 includes a primary beam source 12, a detector 14, and an analyzer 16. Primary beam source 12 may include an X-ray tube that projects a primary beam of X-rays 18 towards a sample 20 that is to be tested. In another exemplary embodiment, primary beam source 12 is a radioactive isotope, which projects a primary beam of gamma rays toward the sample 20. In yet another exemplary embodiment, primary beam source 12 is an electron beam source that projects a primary beam of electrons towards the sample 20. Any suitable radiation source, or plurality of sources, that allow detection system 10 to function as described herein may be used as primary beam source 12.

Sample 20 becomes excited after being exposed to primary beam 18. This excitation causes sample 20 to emit a secondary (i.e., characteristic or fluorescent) radiation 22. Secondary radiation 22 is collected by detector 14. Detector 14 includes electronic circuitry, which is sometimes referred to as a preamplifier, that converts collected secondary radiation to a detector signal 24 (i.e., a voltage signal or an electronic signal) and provides the detector signal 24 to analyzer 16. In at least one embodiment, analyzer 16 includes a digital pulse processor or multi-channel analyzer. While illustrated as a non-handheld unit, detection system 10 illustrates the major components that are also utilized in a handheld spectrometer.

Figure 2:
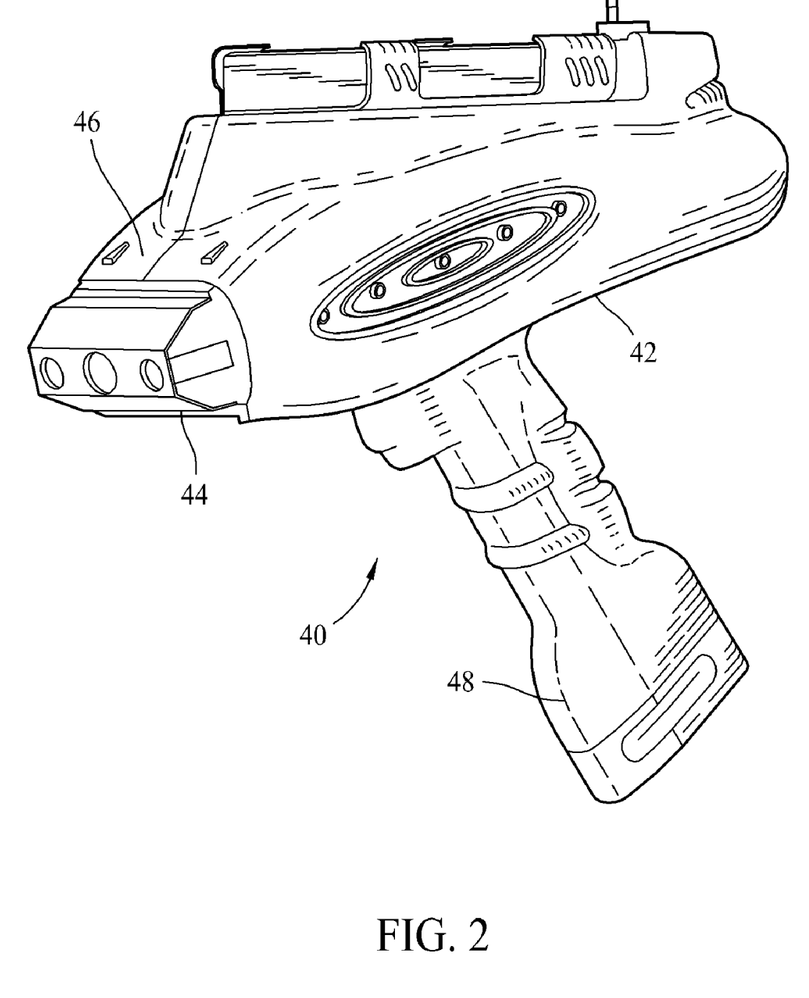
FIG. 2 is perspective view of an exemplary embodiment of a handheld instrument, for example, a handheld X-ray fluorescence (XRF) spectrometer.

FIG. 2 is perspective view of an exemplary embodiment of a handheld instrument, for example, a handheld XRF spectrometer 40. Handheld XRF spectrometer 40 includes a housing 42. Housing 42 encloses and protects the internal assemblies of handheld XRF spectrometer 40.

Housing 42 of handheld XRF spectrometer 40 includes a nosepiece 44 and a body 46. In an exemplary embodiment, housing 42 may have a "handgun-shaped" profile, with a handle 48, extending from body 46. Handle 48 may be positioned such that a user may comfortably hold handle 48 and direct nosepiece 44 to a desired position. Handheld XRF spectrometer 40 includes components similar to those described with respect to FIG. 1, including a detector, a beam source, and an analyzer.

In an exemplary embodiment, housing 42 may be composed of one, or a combination of the following: ABS plastics, and alloy materials such as Magnesium, Titanium, and Aluminum. Housing 42 may be composed of any material with the strength to encase and protect the internal components of handheld XRF spectrometer 40. This protection may include, but is not limited to, protection from elements such as wind and rain, protection from dust and other impurities, and protection from damage caused by dropping spectrometer 40 onto a surface or from rough handling of spectrometer 40. This protection may also be bolstered through the use of over molding, rubber bumpers, shock absorbing mounts internal to the instrument assembly, and/or the use of crushable impact guards.

In one embodiment, housing 42 is composed of lightweight materials, as when in use, handheld XRF spectrometer 40 is held by one of a user's hands. A light-weight handheld XRF spectrometer 40 increases maneuverability and increases the ease-of-use of handheld XRF spectrometer 40 over a heavier handheld spectrometer.

Figure 3:
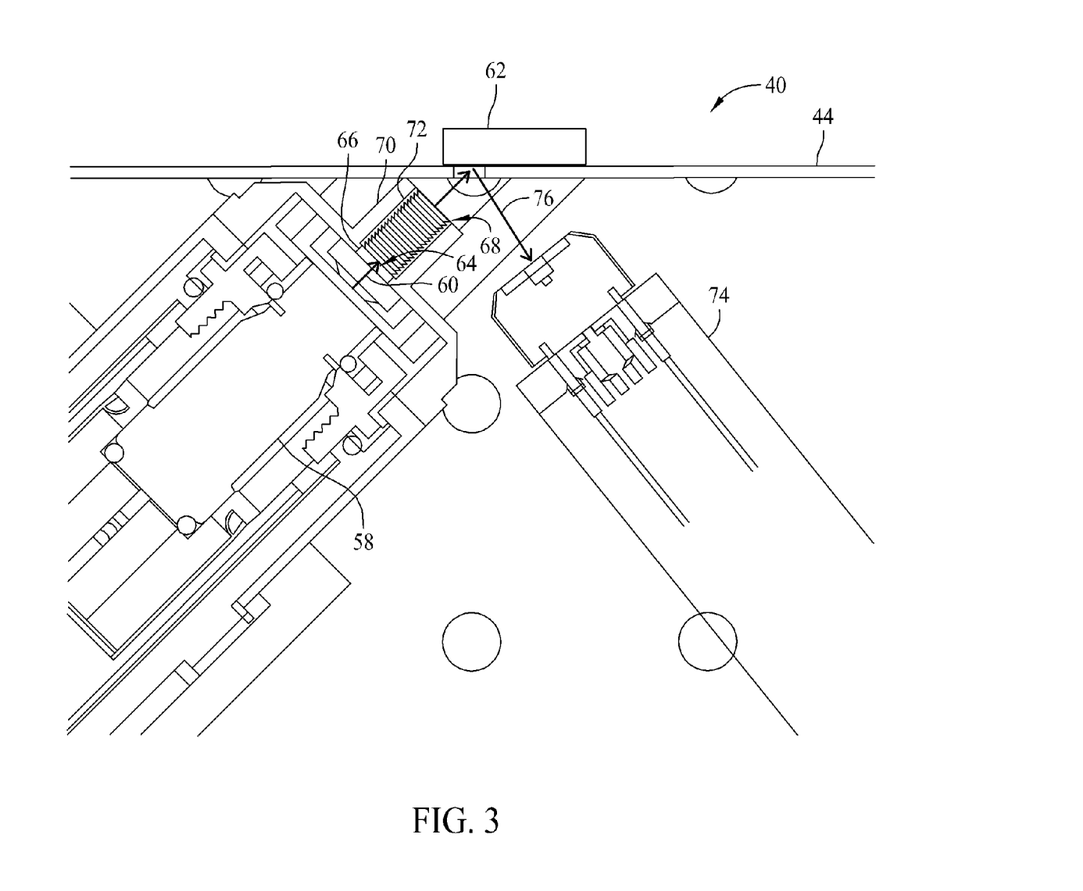
FIG. 3 is a schematic diagram of an exemplary embodiment of a handheld instrument, for example, the handheld XRF spectrometer shown in FIG. 2.

FIG. 3 is a schematic diagram of an exemplary embodiment of a handheld instrument, for example, handheld XRF spectrometer 40 (shown in FIG. 2). A radiation source 58 is positioned adjacent to, or at least partially within, nosepiece 44. Radiation source 58 may include, but is not limited to, an electron beam source, a radioisotope source, a pyroelectric source, and an X-ray tube. In at least some embodiments, radiation source 58 directs a primary X-ray beam 60 toward a sample 62, which is in a position to be tested. Primary X-ray beam 60 may be directed through a slit or opening 64 included within a plate 66. Primary X-ray beam 60 may also be directed through an opening 68 defined by, for example, a tube 70 (also referred to herein as a shielding pipe). Opening 64 and opening 68 at least partially collimate primary X-ray beam 60 and/or reduce scatter of X-ray beam 60.

In the exemplary embodiment, spectrometer 40 also includes a primary beam collimating device 72. X-ray beam 60 is directed through primary beam collimating device 72. Collimating device 72 may be positioned within tube 70 and/or coupled to radiation source 58 or plate 66 in any suitable manner that allows spectrometer 40 to function as described herein. In the exemplary embodiment, collimating device 72 at least partially collimates X-ray beam 60. A collimated beam of X-rays is a beam whose X-rays are nearly parallel and therefore, the beam will spread slowly as it propagates. Collimating device 72 allows X-rays, of X-ray beam 60, oriented in a particular manner, to pass through and irradiate sample 62.

A detector 74 is also positioned adjacent to, or at least partially within, nosepiece 44. After sample 62 is exposed to primary X-ray beam 60, the material of sample 62 is excited and secondary radiation 76 is emitted from sample 62. Secondary radiation 76 is detected by detector 74. By at least partially collimating X-ray beam 60, unwanted scattered radiation reaching detector 74 is reduced. Detector 74 may include, but is not limited to, one of a silicon pin detector, a cadmium telluride detector, a mercuric iodide detector, and a silicon drift detector (SDD). Spectrometer 40 also includes a preamplifier (not shown in FIG. 3). The preamplifier amplifies voltage signals produced by detector 74 that correspond to the secondary radiation 76 received by detector 74. The preamplifier also provides the voltage signals to an analyzer (not shown in FIG. 3) for processing.

Figure 4:
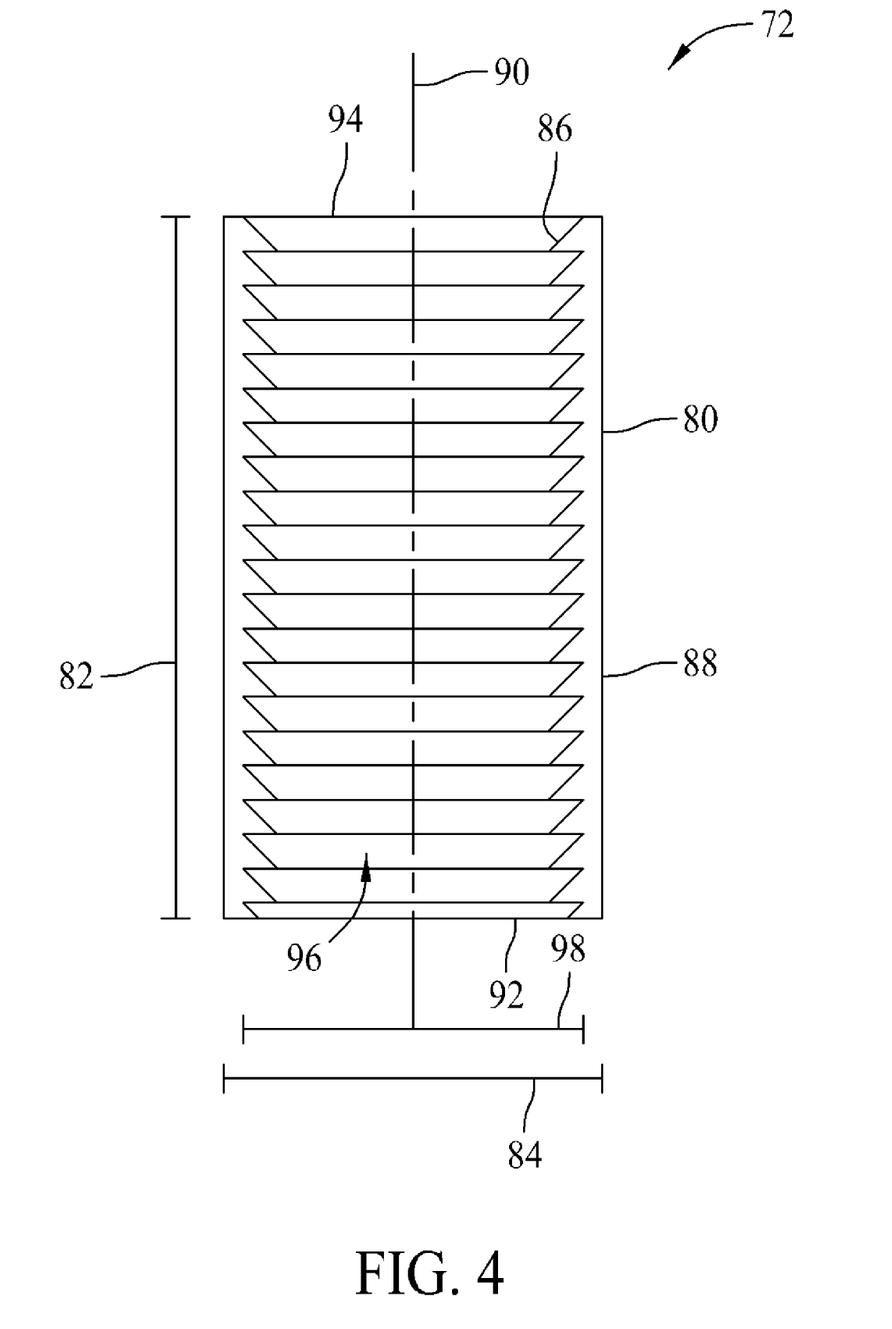
FIG. 4 a cut-away view of an exemplary embodiment of a collimating device that may be included in the handheld XRF spectrometer shown in FIG. 2.

FIG. 4 is a cut-away view of collimating device 72 (shown in FIG. 3). Collimating device 72 is primarily intended for use in a portable XRF instrument, but may be included within other instruments which can benefit from collimation and/or reduced scattering. In the exemplary embodiment, collimating device 72 includes a housing 80 having a length 82 and a diameter 84. Housing 80 includes an interior surface 86 and an exterior surface 88. In the exemplary embodiment, housing 80 is generally cylindrical, centered about a longitudinal center axis 90. In alternative embodiments, housing 80 may include any suitable shape that allows spectrometer 40 to function as described herein. In certain embodiments, collimating device 72 is configured to be positioned within tube 70 (shown in FIG. 3), facilitating improved collimation of primary X-ray beam 60 when compared to spectrometer 40 without collimating device 72. In other embodiments, housing 80 is integrated with tube 70 and/or coupled to plate 66 in any suitable manner that allows spectrometer 40 to function as described herein. Housing 80 includes an inlet 92 and an outlet 94, and a cavity 96 extending between inlet 92 and outlet 94. Inlet 92 is configured to receive primary X-ray beam 60 (shown in FIG. 3) and outlet 94 is configured to output a collimated beam toward sample 62 (shown in FIG. 3). In the exemplary embodiment, cavity 96 is an internal volume that is cylindrical-shaped, having a varying internal diameter 98. Cavity 96 is also referred to herein as an opening extending between inlet 92 and outlet 94. In the exemplary embodiment, interior surface 86 of housing 80 includes a plurality of ridges, extending from interior surface 86 radially toward center axis 90. The plurality of ridges, also referred to herein as rings, form alternating parallel grooves and ridges.

Figure 5:
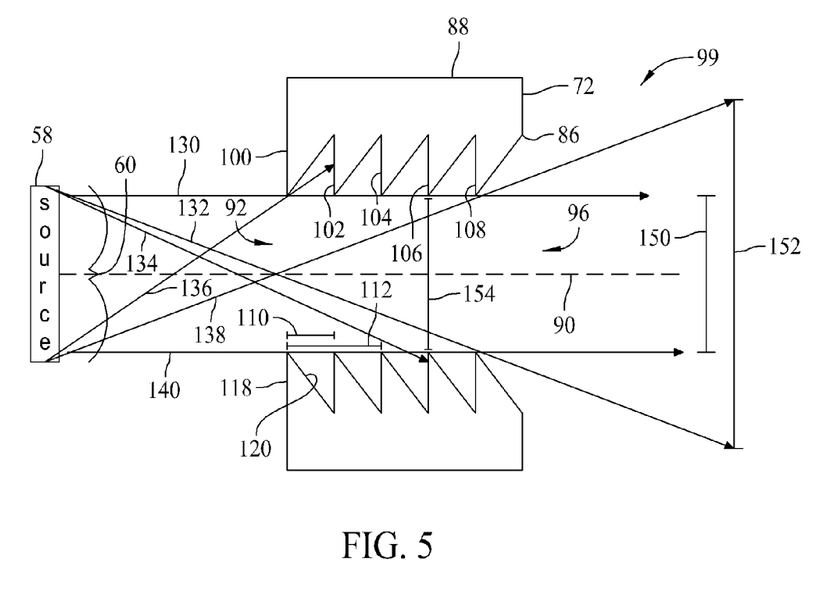
FIG. 5 is a cross-sectional view of the collimating device shown in FIG. 4.

FIG. 5 is a cross-sectional view of an exemplary radiation source and collimating system 99. In the exemplary embodiment, system 99 includes a collimating device and a radiation source 58, for example, collimating device 72 and radiation source 58. Collimating device 72 is formed from a material that reflects and/or absorbs X-ray radiation. In the exemplary embodiment, collimating device 72 includes a first circumferential ridge 100, a second circumferential ridge 102, a third circumferential ridge 104, a fourth circumferential ridge 106, and a fifth circumferential ridge 108. Ridges 100, 102, 104, 106, and 108 extend from interior surface 86 radially toward longitudinal center axis 90. In the exemplary embodiment, ridges 100, 102, 104, 106, and 108 share a center (i.e., center axis 90). Each successive ridge is a greater distance from inlet 92 than the previous ridge. For example, second ridge 102 is a first distance 110 from inlet 92 and third ridge 104 is a second distance 112 from inlet 92, wherein second distance 112 is larger than first distance 110. Each of ridges 100, 102, 104, 106, and 108 is substantially parallel to all of the other ridges. Furthermore, a plane that includes each individual ridge 100, 102, 104, 106, and 108 is substantially perpendicular to center axis 90.

In the exemplary embodiment, each of ridges 100, 102, 104, 106, and 108 includes a triangular cross-section having a first edge 118 substantially perpendicular to center axis 90. Each of ridges 100, 102, 104, 106, and 108 also includes a second edge 120, which forms a substantially saw-tooth cross-sectional profile to ridges 100, 102, 104, 106, and 108. Such a saw-tooth cross-section facilitates ease in manufacturing collimating device 72. Although described as saw-tooth in cross-section, any other shape may be used that allows collimating device 72 to function as described herein. For example, ridges 100, 102, 104, 106, and 108 may include a cross-section having any shape where second edge 120 does not have a direct view of radiation source 58 and first edge 118 does not have a direct view of sample 62.

As described above, radiation source 58 generates primary X-ray beam 60. Primary X-ray beam 60 includes individual X-rays, for example, a first X-ray 130, a second X-ray 132, a third X-ray 134, a fourth X-ray 136, a fifth X-ray 138, and a sixth X-ray 140. In the example illustrated, first X-ray 130 and sixth X-ray 140 are collimated. In other words, first X-ray 130 is substantially parallel to sixth X-ray 140, and X-rays 130 and 140 are substantially perpendicular to source 58. Second X-ray 132 and fifth X-ray 138 are not well collimated. Third X-ray 134 and fourth X-ray 136 are stopped by collimating device 72. X-rays 130 and 140 define a beam width 150. X-rays that exit collimating device 72 outside of beam width 150 are referred to herein as scatter or divergent. For example, second X-ray 132 and fifth X-ray 138 are not included within beam width 150, and define a maximum divergent width 152. Beam width 150 is substantially defined by a diameter 154 of ridges 100, 102, 104, 106, and 108. In the exemplary embodiment, each of ridges 100, 102, 104, 106, and 108 has diameter 154. In an alternative embodiment, a diameter of ridges 100, 102, 104, 106, and 108 increases as ridges 100, 102, 104, 106, and 108 increase in distance from source 58. For example, ridge 100 may have a smaller diameter than ridge 108. Each individual ridge 100, 102, 104, 106, and 108 may have any diameter that allows collimating device 72 to function as described herein. Ridges 100, 102, 104, 106, and 108 act as slits or apertures that facilitate reducing scatter while maintaining an acceptable level of collimation which will lessen the occurrence of unwanted Bragg, Rayliegh, and Compton peaks in XRF instruments. Collimating device 72 facilitates increasing collimation of X-ray beam 60 and therefore, reducing scatter width 152.

Figure 6:
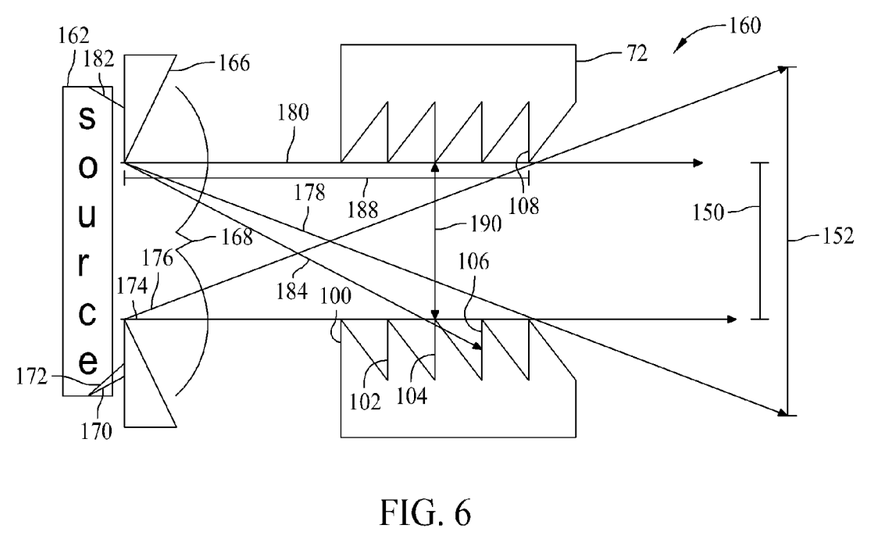
FIG. 6 is a cross-sectional view of an alternative embodiment of the collimating device shown in FIG. 5.

FIG. 6 is a cross-sectional view of an alternative embodiment 160 of collimating system 99 (shown in FIG. 5). Collimating system 160 includes collimating device 72, a radiation source 162, and a first slit 166. In the alternative embodiment, first slit 166 is positioned adjacent to radiation source 162. In comparison to radiation source 58 (shown in FIG. 5), radiation source 162 generates a wider beam of radiation 168. Beam 168 includes a plurality of individual X-rays, for example, a first X-ray 170, a second X-ray 172, a third X-ray 174, a fourth X-ray 176, a fifth X-ray 178, a sixth X-ray 180, a seventh X-ray 182, and an eighth X-ray 184. In the exemplary embodiment, first slit 166 includes a material that reflects and/or absorbs X-ray radiation. For example, first slit 166 absorbs and/or reflects first X-ray 170, second X-ray 172, and seventh X-ray 182, thereby preventing X-rays 170, 172, and 182 from exiting collimating device 72. Collimating device 72 absorbs and/or reflects eighth X-ray 184. The combination of first slit 166 and collimating device 72 enhances collimation of beam 168. The larger a distance 188 between first slit 166 and the slit defined by ridge 108, the greater a provided level of collimation. If slit 166 is not present, but a smallest diameter 190 of the plurality of ridges 100, 102, 104, 106, and 108 is of similar size to radiation source 162, then similar collimation is achieved.

Figure 7:
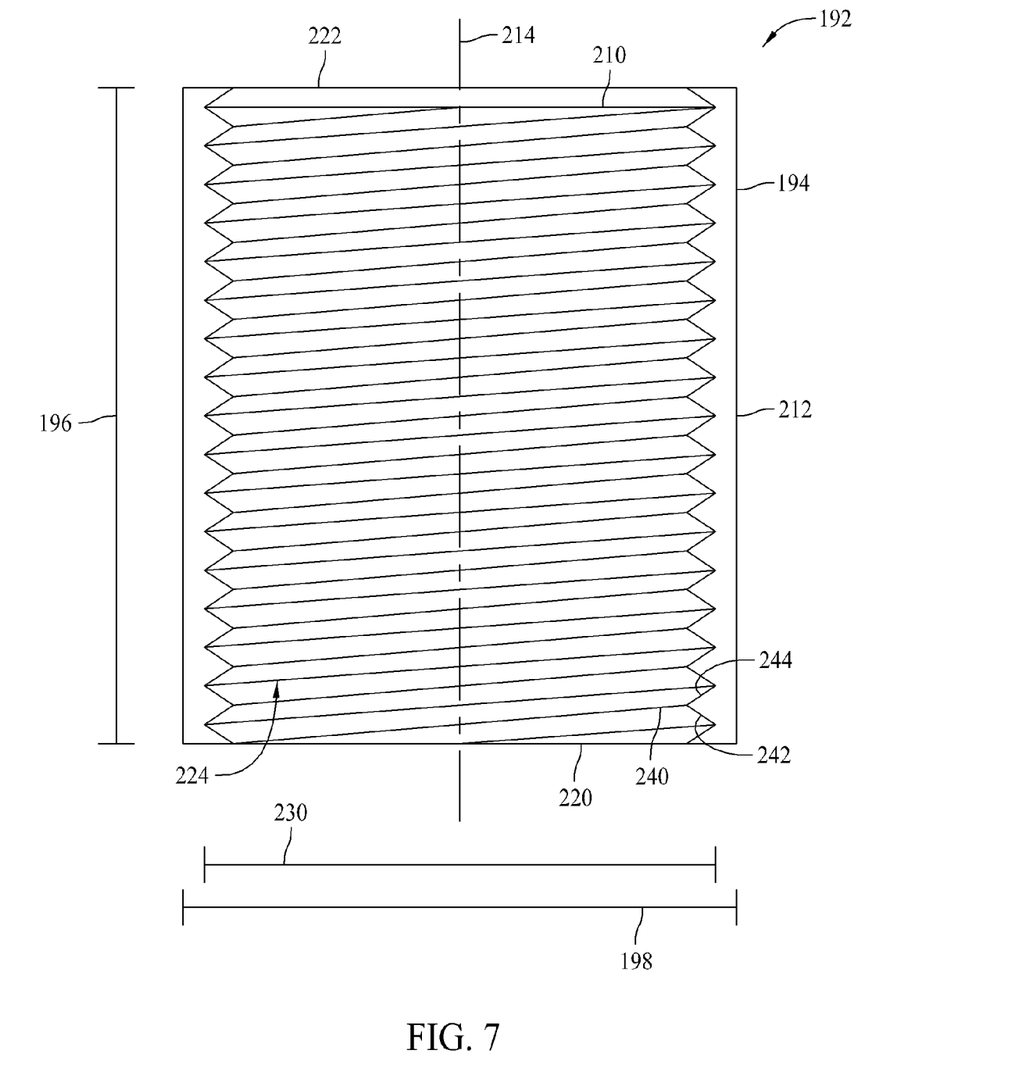
FIG. 7 is a cut-away view of an alternative embodiment of a collimating device that may be included in the handheld XRF spectrometer shown in FIG. 2.

FIG. 7 is a cut-away view of an alternative embodiment of a collimating device 192 that may be included within handheld XRF spectrometer 40 (shown in FIG. 2). In the alternative embodiment, collimating device 192 includes a housing 194 having a length 196 and a diameter 198. Housing 194 includes an interior surface 210 and an exterior surface 212. Housing 194 is generally cylindrical, centered about a longitudinal center axis 214. Housing 194 includes an inlet 220 and an outlet 222, and a cavity 224 extending between inlet 220 and outlet 222. Inlet 220 is configured to receive primary X-ray beam 60 (shown in FIG. 3) and outlet 222 is configured to output a collimated beam toward sample 62 (shown in FIG. 3). In the exemplary embodiment, cavity 224 is an internal volume that is cylindrical-shaped, having a varying internal diameter 230. Cavity 224 is also referred to herein as an opening extending between inlet 220 and outlet 222.

In the alternative embodiment, collimating device 192 includes a single spiraling ridge 240 continuous from inlet 220 to outlet 222. Spiraling ridge 240 may also be referred to herein as a thread. Spiraling ridge 240 includes at least a first surface 242 and a second surface 244. X-ray radiation incident upon first surface 242 is either reflected or absorbed. First surface 242 may be substantially perpendicular to radiation applied to collimating device 192 at inlet 220. Spiraling ridge 240 is similar to an internal thread of a fastening device, for example, a nut. Spiraling ridge 240 may have a square cross-sectional shape, a triangular cross-sectional shape, a trapezoidal cross-sectional shape, or any other shape that allows collimating device 192 to function as described herein. Unlike ridges 100, 102, 104, 106, and 108 (shown in FIGS. 5 and 6), spiraling ridge 240 does not form a plurality of slits or apertures that are perpendicular to longitudinal center axis 214. However, first surface 242 of spiraling ridge 240 collimates an X-ray beam in substantially the same manner as collimating device 72. Collimating device 192 may be manufactured using a cutting tool, for example, a tap. Collimating device 192 may be any length 196, and may be particularly useful as length 196 increases due to ease in manufacturing.

Figure 8:
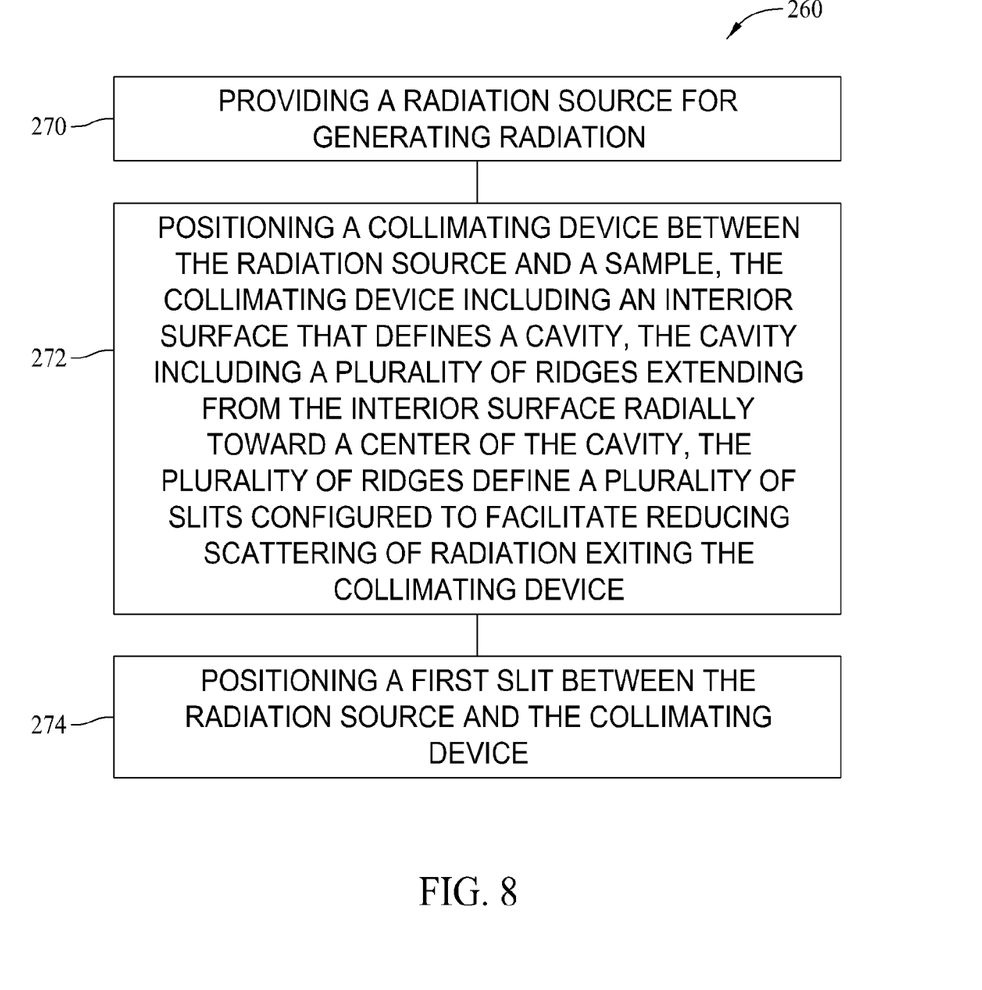
FIG. 8 is a flow chart of an exemplary method for collimating radiation, for example, radiation generated by the radiation source shown in FIG. 3.

FIG. 8 is a flow chart 260 of an exemplary method for collimating radiation, for example, radiation generated by radiation source 58 (shown in FIG. 3). In the exemplary embodiment, the exemplary method includes providing 270 a radiation source, for example, radiation source 58, for generating radiation, for example, primary X-ray beam 60 (shown in FIG. 3). The method may also include positioning 272 a collimating device, for example, collimating device 72 (shown in FIG. 3), between radiation source 58 and a sample, for example, sample 62 (shown in FIG. 3). In the exemplary embodiment, collimating device 72 includes an interior surface 86 (shown in FIG. 4) that defines cavity 96 (shown in FIG. 4). In the exemplary embodiment, cavity 96 includes a plurality of ridges extending from interior surface 86 radially toward center axis 90 of cavity 96. The plurality of ridges define a plurality of slits configured to facilitate reducing scattering of radiation exiting collimating device 72. In the exemplary embodiment, collimating device 72 is a single part configured to fit substantially within a shielding pipe of a portable instrument, for example, but not limited to, a portable X-ray fluorescence instrument.

In an alternative embodiment, the method also includes positioning 274 a first slit, for example, first slit 166 (shown in FIG. 6), between radiation source 58 and collimating device 72. First slit 166 further collimates the generated radiation (i.e., primary X-ray beam 60). The larger a distance between first slit 166 and an opposite end of collimating device 72, relative to the slit width, the greater a level of collimation produced by the first slit/collimating device combination.

Described herein are exemplary methods, systems, and devices for performing an analysis of a substance using a portable spectrometer. More specifically, the methods, systems, and devices described herein facilitate reducing scatter of radiation applied to a sample during testing of the sample without increasing a distance between a radiation source and the sample. A reduction in scattered radiation facilitates reducing unwanted Bragg peaks, reducing XRF, Compton and/or Rayleigh back scatter, and reducing excitation of atoms present in the instrument that may result in fluorescence detectable by the detector. Maintaining the distance between the radiation source and the sample prevents having to increase the power provided to the radiation source to counteract the additional distance needed to apply collimation of the radiation applied to the sample.

The methods, systems, and devices described herein facilitate efficient and economical examination of a sample material. The methods, systems, and devices described herein allow for a series of slits to be machined as a single part and inserted into a larger tube without using special alignment procedures. Exemplary embodiments of methods, systems, and devices are described and/or illustrated herein in detail. The methods, systems, and devices are not limited to the specific embodiments described herein, but rather, components of each system, as well as steps of each method, may be utilized independently and separately from other components and steps described herein. Each component, and each method step, can also be used in combination with other components and/or method steps.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A collimating device comprising:
a collimator housing defining an interior surface and an exterior surface of said collimating device, said collimator housing comprising an inlet and an outlet and a cavity extending between said inlet and said outlet; and
a plurality of sawtooth ridges extending radially inward from the interior surface of said collimator housing toward a center axis of said cavity, each said ridge comprising a first edge substantially perpendicular to the center axis and a second edge sloping radially outward away from the inlet, said plurality of ridges form a plurality of slits within said cavity configured to collimate radiation entering said inlet and exiting said outlet.

2. A device in accordance with claim 1, wherein said housing is substantially cylindrical.

3. A device in accordance with claim 1, wherein said plurality of slits are substantially circular, having substantially equal diameters.

4. A device in accordance with claim 1, wherein said plurality of slits are substantially circular, having diameters that increase as a distance from said inlet increases.

5. A device in accordance with claim 1, wherein said plurality of ridges have a substantially triangular cross-section.

6. A device in accordance with claim 1, wherein each of said plurality of ridges comprises a first edge substantially perpendicular to radiation applied to said collimating device at said inlet.

7. A device in accordance with claim 1 further comprising a single slit positioned between a radiation source and said inlet, said single slit configured to further collimate the provided radiation.

8. A device in accordance with claim 1, wherein said housing is configured to fit at least partially within a shielding pipe of a portable instrument.

9. A device in accordance with claim 1, wherein said housing includes radiation reflecting material or radiation absorbing material.

10. A method of collimating radiation output by a radiation source, said method comprising:
providing a radiation source for generating radiation; and
positioning a collimating device between the radiation source and a sample, the collimating device comprising an interior surface that defines a cavity, the cavity including a plurality of ridges having a sawtooth cross-section extending from the interior surface toward a center of the cavity, each ridge defined by a first edge extending perpendicularly from the interior surface toward a center axis of the cavity and a second edge sloping radially away from the first edge, the plurality of ridges defining a plurality of slits configured to facilitate reducing scattering of radiation exiting the collimating device.

11. A method in accordance with claim 10, wherein positioning a collimating device further comprises positioning a single part configured to fit substantially within a shielding pipe of a portable instrument.

12. A method in accordance with claim 11, wherein the portable instrument comprises a portable X-ray fluorescence instrument.

13. A method in accordance with claim 10 further comprising positioning a first slit between the radiation source and the collimating device, the first slit configured to further collimate the generated radiation.

14. A detection system comprising:
a portable housing;
a radiation source at least partially enclosed in the portable housing and configured to generate a primary radiation and impinge the primary radiation onto a sample, the primary radiation configured to excite the sample and cause the sample to reflect a secondary radiation;
a radiation detector at least partially enclosed in the portable housing and configured to detect the secondary radiation; and
a collimating device positioned between the radiation source and the sample, the collimating device comprising a housing that includes a cavity extending between an inlet and an outlet of the collimating device, the collimating device comprising a plurality of sawtooth ridges extending from the housing toward a center axis of the cavity, the plurality of ridges defining a plurality of slits configured to facilitate reducing scattering of radiation exiting the outlet of the collimating device.

15. A detection system in accordance with claim 14 further comprising an instrument housing configured to at least partially enclose the radiation source, the radiation detector, the collimating device, and a portable power supply.

16. A detection system in accordance with claim 14, wherein a diameter of the plurality of slits is substantially equal.

17. A detection system in accordance with claim 14, wherein a diameter of the plurality of slits increases as the ridges increase in distance from the inlet.

18. A detection system in accordance with claim 14, wherein the plurality of ridges include a substantially triangular cross-section.

19. A detection system in accordance with claim 14, wherein the collimating device is coupled to at least one of the radiation source and a shielding pipe of the detection system.

20. A detection system in accordance with claim 14 further comprising a first slit positioned between the radiation source and the collimating device, the first slit configured to further collimate the generated radiation.

21. A collimating device comprising:
a housing defining an interior surface and an exterior surface of said collimating device, said housing comprising an inlet and an outlet and a cavity extending between said inlet and said outlet; and
a spiraling ridge extending from the interior surface of said housing toward a center of said cavity, said spiraling ridge beginning at said inlet and ending at said outlet, said spiraling ridge including a first surface configured to collimate radiation entering said inlet and exiting said outlet.

22. A device in accordance with claim 21, wherein said housing is substantially cylindrical.

23. A device in accordance with claim 21, wherein said spiraling ridge has a substantially square cross-sectional shape, triangular cross-sectional shape, or trapezoidal cross-sectional shape.

24. A device in accordance with claim 21, wherein said first surface is substantially perpendicular to radiation applied to said collimating device at said inlet.

25. A device in accordance with claim 21, wherein said housing is configured to fit at least partially within a shielding pipe of a portable instrument.

* * * * *